(12) United States Patent
Krizan

(10) Patent No.: US 11,364,347 B2
(45) Date of Patent: Jun. 21, 2022

(54) ELECTRONIC PLUNGER ASSEMBLY

(71) Applicant: West Pharmaceutical Services, Inc., Exton, PA (US)

(72) Inventor: Jason Krizan, Ellicott City, MD (US)

(73) Assignee: West Pharmaceutical Services, Inc., Exton, PA (US)

(*) Notice: Subject to any disclaimer, the term of this patent is extended or adjusted under 35 U.S.C. 154(b) by 0 days.

(21) Appl. No.: 17/279,745

(22) PCT Filed: Oct. 18, 2019

(86) PCT No.: PCT/US2019/056871
§ 371 (c)(1),
(2) Date: Mar. 25, 2021

(87) PCT Pub. No.: WO2020/081897
PCT Pub. Date: Apr. 23, 2020

(65) Prior Publication Data
US 2021/0308382 A1 Oct. 7, 2021

Related U.S. Application Data

(60) Provisional application No. 62/747,740, filed on Oct. 19, 2018.

(51) Int. Cl.
*A61M 5/315* (2006.01)
(52) U.S. Cl.
CPC . *A61M 5/31513* (2013.01); *A61M 2205/0216* (2013.01); *A61M 2205/50* (2013.01)

(58) Field of Classification Search
CPC ...... A61M 5/31513; A61M 2205/0216; A61M 2205/50; A61M 5/31511; A61M 5/1452;
(Continued)

(56) References Cited

U.S. PATENT DOCUMENTS

2001/0034506 A1 10/2001 Hirschman et al.
2004/0078993 A1 4/2004 Vetter et al.
(Continued)

FOREIGN PATENT DOCUMENTS

CN 102307605 A 1/2012
CN 103874522 A 6/2014
(Continued)

OTHER PUBLICATIONS

Int'l Preliminary Report on Patentability dated Sep. 22, 2020 in Int'l Application No. PCT/US2019/056871.
(Continued)

*Primary Examiner* — Bhisma Mehta
*Assistant Examiner* — Nidah Hussain
(74) *Attorney, Agent, or Firm* — BakerHostetler

(57) ABSTRACT

A plunger assembly is configured for slidable advancement through a reservoir of a vessel containing a material to be administered. The plunger assembly includes a plunger rod having a distal end configured to be inserted into the reservoir. An elastomeric plunger extending from the distal end of the plunger rod is configured to sealingly engage a sidewall of the reservoir. At least one printed circuit board is embedded within the plunger, and at least one electronic component is electrically connected with the at least one printed circuit board.

20 Claims, 9 Drawing Sheets

(58) Field of Classification Search
CPC .. A61M 5/315; A61M 5/281; A61M 5/14526; A61M 5/145; A61M 5/1422; A61M 60/258; A61M 2005/3152
USPC .......................................................... 604/218
See application file for complete search history.

(56) References Cited

U.S. PATENT DOCUMENTS

| | | | |
|---|---|---|---|
| 2006/0072868 A1* | 4/2006 | Bateman | G01F 23/14 385/12 |
| 2008/0106388 A1* | 5/2008 | Knight | A61M 5/31511 340/10.42 |
| 2014/0249410 A1* | 9/2014 | Uber, III | A61M 5/20 604/246 |
| 2015/0217059 A1 | 8/2015 | Ashby et al. | |
| 2017/0312430 A1 | 11/2017 | Schleicher et al. | |
| 2017/0312445 A1* | 11/2017 | Mirov | B23P 15/00 |
| 2018/0054912 A1 | 2/2018 | Hannig | |

FOREIGN PATENT DOCUMENTS

| | | |
|---|---|---|
| JP | 06-013541 A | 1/1994 |
| JP | 2006-156574 A | 6/2006 |
| JP | 2011-155097 A | 8/2011 |

OTHER PUBLICATIONS

Int'l Search Report and Written Opinion dated Feb. 5, 2020 in Int'l Application No. PCT/US2019/056871.

* cited by examiner

ELECTRONIC PLUNGER ASSEMBLY

CROSS-REFERENCE TO RELATED APPLICATIONS

This application is a section 371 of International Application PCT/US2019/056871, filed Oct. 18, 2019, which was published on Apr. 23, 2020 under Publication No. WO 2020/081897 A1, and which claims priority from U.S. Provisional Patent Application No. 62/747,740, titled "Plunger for Electronic Circuits And Methods of Manufacture Thereof", filed on Oct. 19, 2018, the entire contents of which are incorporated by reference herein.

BACKGROUND OF THE DISCLOSURE

The present disclosure is generally directed to plunger assemblies, and, more particularly, to plunger assemblies having a printed circuit board within.

Plungers that are configured for slidable advancement through a reservoir of a vessel containing a material to be administered are commonly used. Generally, plungers are formed of an elastomeric material, enabling slidable advancement of the plunger while maintaining a seal between the plunger the inner sidewall of the reservoir. One drawback of conventional plungers is that they often exhibit a relatively large footprint in return for performing the sole function of providing a seal at a proximal end of a reservoir and assist in ejecting the material from the reservoir.

Generally, the interior of the plunger defines a relatively large, otherwise unused space. Accordingly, there is a need for improved plungers.

BRIEF SUMMARY OF THE DISCLOSURE

Briefly stated, one aspect of the present disclosure is directed to a plunger assembly configured for slidable advancement through a reservoir of a vessel containing a material to be administered. The plunger assembly includes a plunger rod having a distal end configured to be inserted into the reservoir. An elastomeric plunger extending from the distal end of the plunger rod is configured to sealingly engage a sidewall of the reservoir. At least one printed circuit board is embedded within the plunger and secured to the distal end of the plunger rod, and at least one electronic component is electrically connected with the at least one printed circuit board.

Briefly stated, another aspect of the present disclosure is directed to a plunger assembly configured for slidable advancement through a reservoir of a vessel containing a material to be administered. The plunger assembly includes a plunger rod having a distal end configured to be inserted into the reservoir. An elastomeric plunger extending from the distal end of the plunger rod is configured to sealingly engage a sidewall of the reservoir. At least one printed circuit board is embedded within the plunger and at least one electronic component is electrically connected with the at least one printed circuit board. The at least one printed circuit board includes at least one of a via and a recess and at least a portion of the elastomeric plunger is disposed within at least one of the via and the recess.

Briefly stated, another aspect of the present disclosure is directed to an elastomeric plunger positioned stationary within a reservoir of a vessel containing a material to be administered. The plunger is configured to sealingly engage a sidewall of the reservoir and includes at least one printed circuit board embedded within the plunger. At least one electronic component is electrically connected with the at least one printed circuit board, and at least one channel extends through the plunger fluidly connected with the reservoir.

BRIEF DESCRIPTION OF THE DRAWINGS

The following detailed description of aspects of the disclosure will be better understood when read in conjunction with the appended drawings. It should be understood, however, that the disclosure is not limited to the precise arrangements and instrumentalities shown. In the drawings.

DETAILED DESCRIPTION OF THE DISCLOSURE

Figure 1:
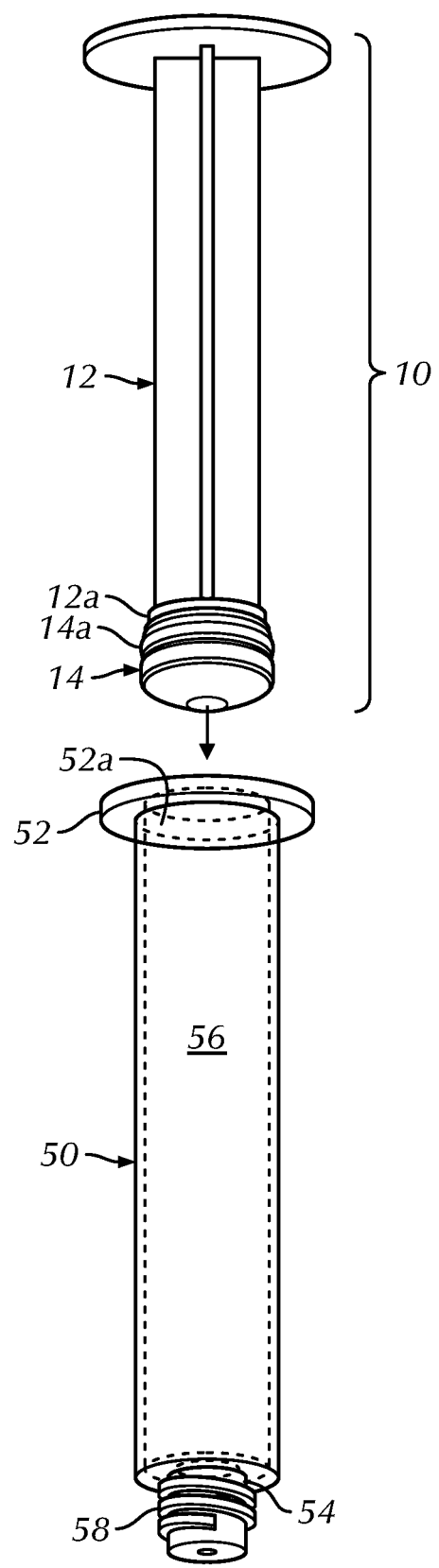
FIG. 1 is a perspective view of a syringe barrel usable with a plunger assembly according to a first embodiment of the present disclosure.

Certain terminology is used in the following description for convenience only and is not limiting. The words "lower," "bottom," "upper" and "top" designate directions in the drawings to which reference is made. The words "inwardly," "outwardly," "upwardly" and "downwardly" refer to directions toward and away from, respectively, the geometric center of the plunger assembly, and designated parts thereof, in accordance with the present disclosure. Unless specifically set forth herein, the terms "a," "an" and "the" are not limited to one element, but instead should be read as meaning "at least one." The terminology includes the words noted above, derivatives thereof and words of similar import.

It should also be understood that the terms "about," "approximately," "generally," "substantially" and like terms, used herein when referring to a dimension or characteristic of a component of the disclosure, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to the drawings in detail, wherein like numerals indicate like elements throughout, there is shown in FIGS.

Figure 2:
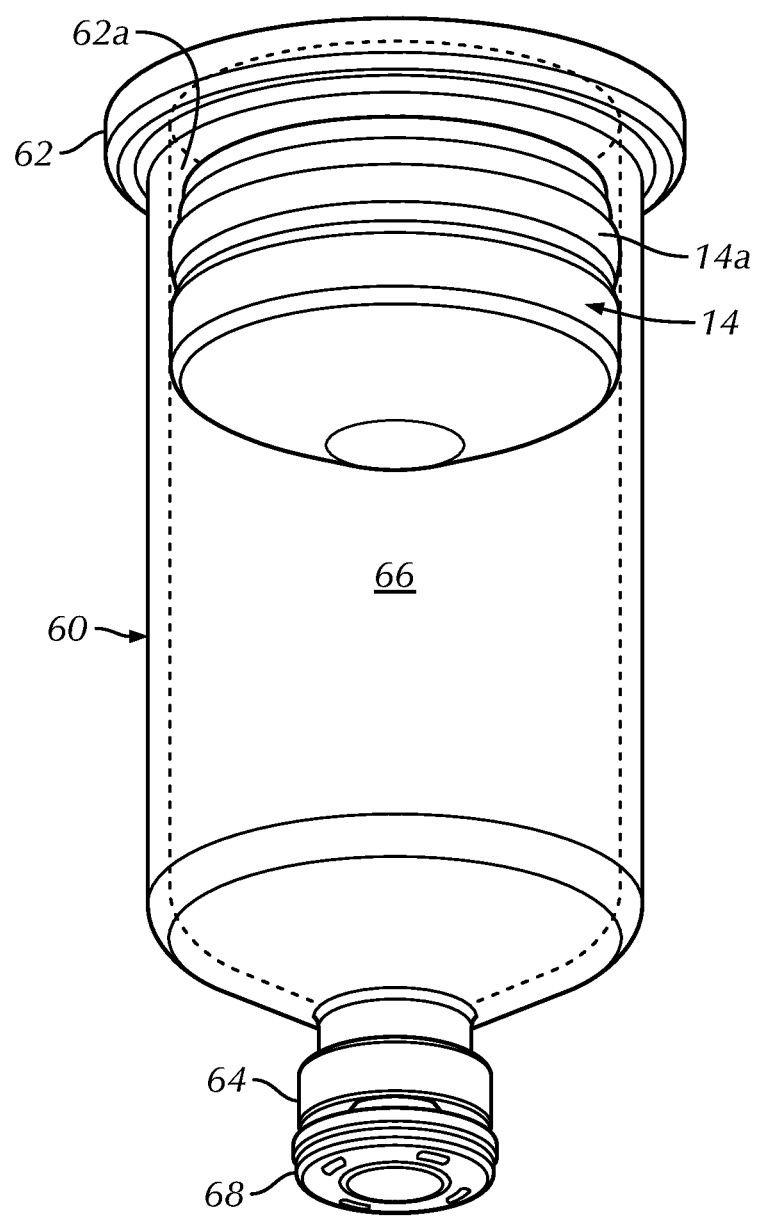
FIG. 2 is a perspective view of a cartridge barrel usable with the plunger assembly according to the first embodiment of the present disclosure.
Figure 7:
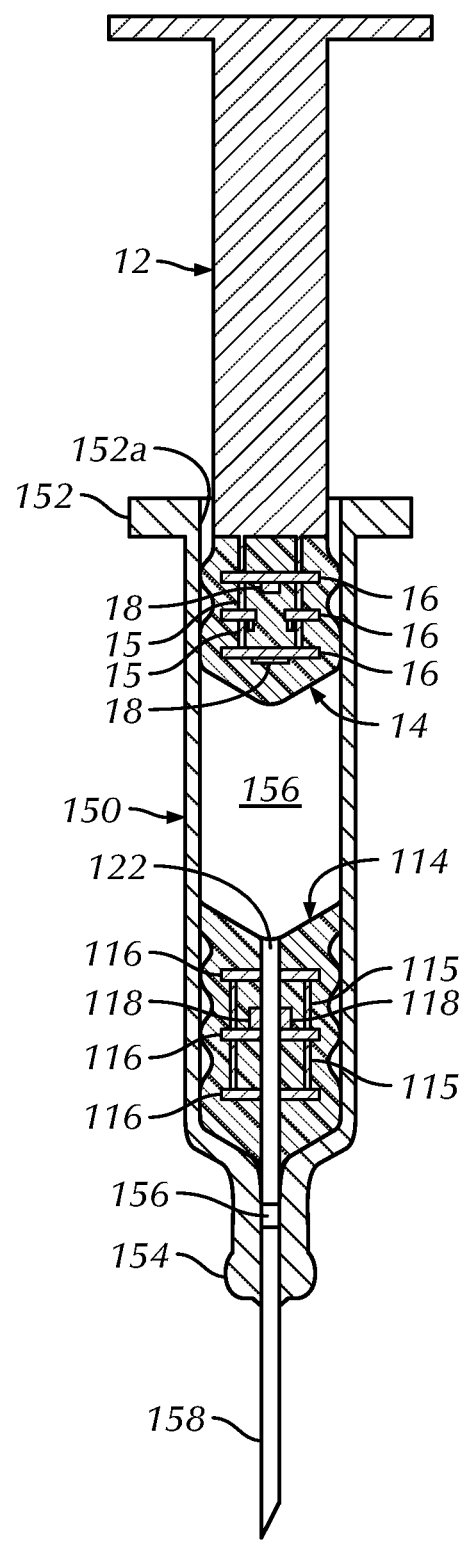
FIG. 7 is a cross-sectional elevational view of a syringe barrel usable with a plunger assembly according to a second embodiment of the present disclosure.

1-6 a plunger assembly 10, in accordance with a first embodiment of the present disclosure, configured for slidable advancement through a reservoir of a vessel containing a material to be administered, as will be described in further detail. In one embodiment, the vessel may take the form of a syringe barrel 50, 150 (FIGS. 1, 7) or a cartridge barrel 60 (FIG. 2), but the disclosure is not so limited. As should be understood by those of ordinary skill in the art, the syringe 50, 150 includes an open proximal end 52, 152, respectively, having an opening 52a, 152a, respectively, an opposing distal end 54, 154, respectively and a reservoir 56, 156, respectively, therebetween. In one configuration, as shown in FIG. 1, the distal end 54 may include a connector 58, e.g., without limitation, a luer connector. In an alternative configuration, as shown in FIG. 7, the distal end 154 may include an injection needle 158 in fluid communication with the reservoir 156, but the disclosure is not so limited to either configuration. Similarly to the syringe 50, 150, and as also should be understood by those of ordinary skill in the art, a cartridge barrel 60 includes an open proximal end 62 having an opening 62a, an opposing distal end 64, and a reservoir 66 therebetween. In the illustrated configuration, the distal end 64 is sealed by a stopper 68, but the disclosure is not so limited.

As shown in FIG. 1, the plunger assembly 10 includes a plunger rod 12 and an elastomeric plunger 14 connected to a distal end 12a of the plunger rod 12 (as will be described in further detail below). As should be understood, the plunger rod 12 is configured to be inserted into the reservoir 56, 156, or 66 of the vessel 50, 150, or 60 (via open end 52a, 152a or 62a), and, in some configurations, to also insert the plunger 14 into the reservoir 56, 156 or 66. The plunger rod 12 is also configured to advance the plunger 14 through the reservoir 56, 156 or 66 in a manner well understood by those of ordinary skill in the art.

As shown in FIGS. 1-6, the elastomeric plunger 14 may be generally tubular, but the disclosure is not so limited. The elastomeric plunger 14 is configured to sealingly engage the sidewall of the reservoir 56, 156, or 66 when inserted therein. For example, in one non-limiting configuration, the elastomeric plunger 14 may include a series of radially outwardly protruding circumferential ridges 14a. An external diameter of the ridges 14a may be sized to create an interference fit with the sidewall of the reservoir 56, 156, or 66, i.e., may be slightly larger than the interior diameter of the reservoir 56, 156, or 66 such that the ridges 14a may be compressed by the sidewall upon insertion of the plunger 14 therein to create a sliding sealed engagement. In some embodiments, the elastomeric plunger 14 may be constructed of a thermoplastic elastomer or a thermoset elastomer, e.g., without limitation, having a Shore A hardness of between 30 and 80. As should be understood, however, the elastomeric plunger 14 may be constructed of different materials, provided they are capable of performing the functions of the plunger 14 described herein. Additionally, materials having a low level of particulates, low bioburden/endotoxin, capable of withstanding standard transit conditions may be utilized.

Figure 3:
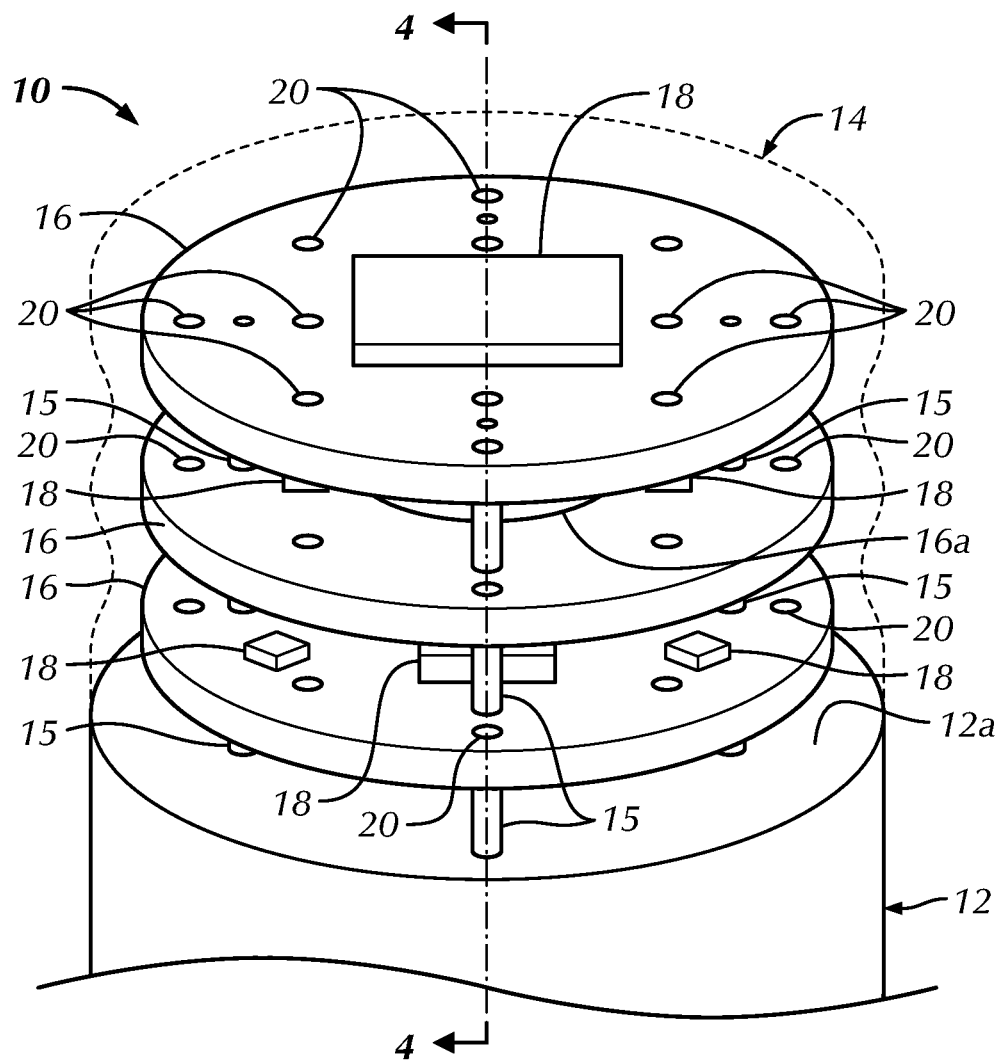
FIG. 3 is an enlarged, partial perspective view of the plunger assembly of FIG. 1, with the printed circuit boards within the plunger being axially spaced.
Figure 4:
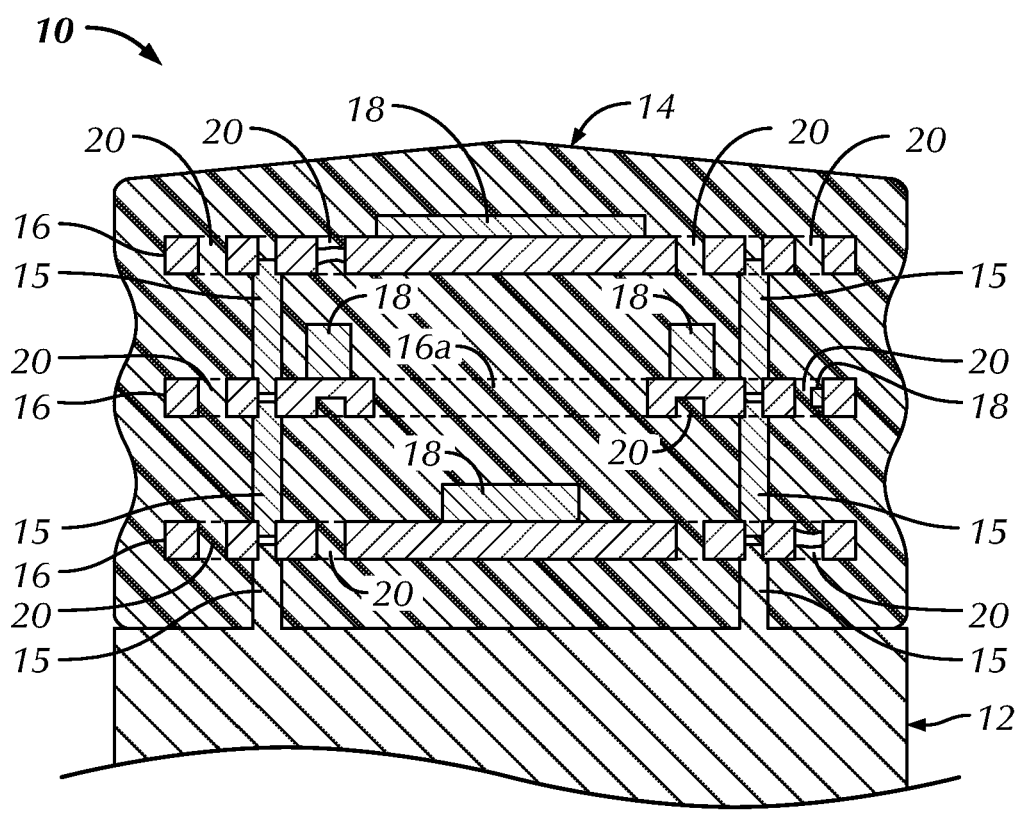
FIG. 4 is a cross-sectional elevational view of the plunger assembly of FIG. 3, taken along sectional line 4-4 of FIG. 3
Figure 5:
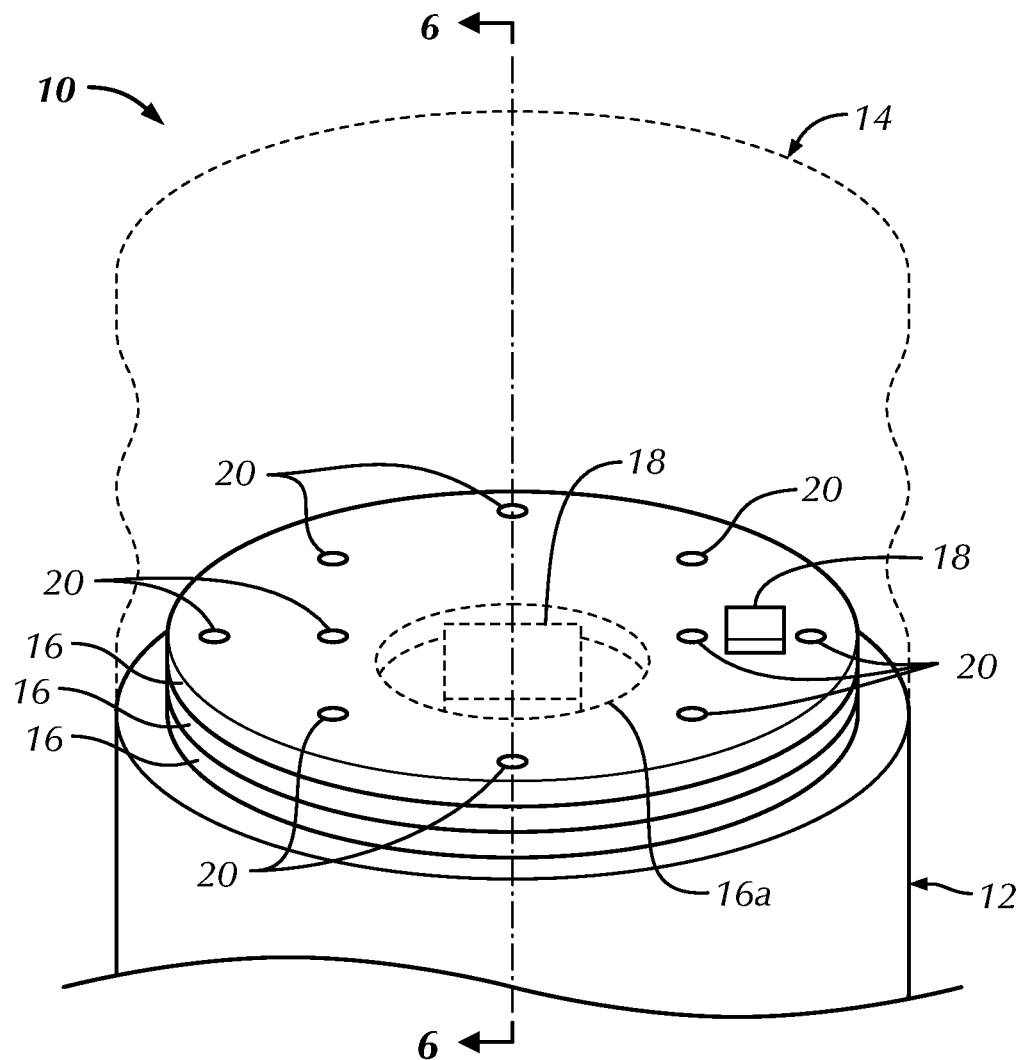
FIG. 5 is an enlarged, partial perspective view of the plunger assembly of FIG. 1, with the printed circuit boards within the plunger being stacked.
Figure 6:
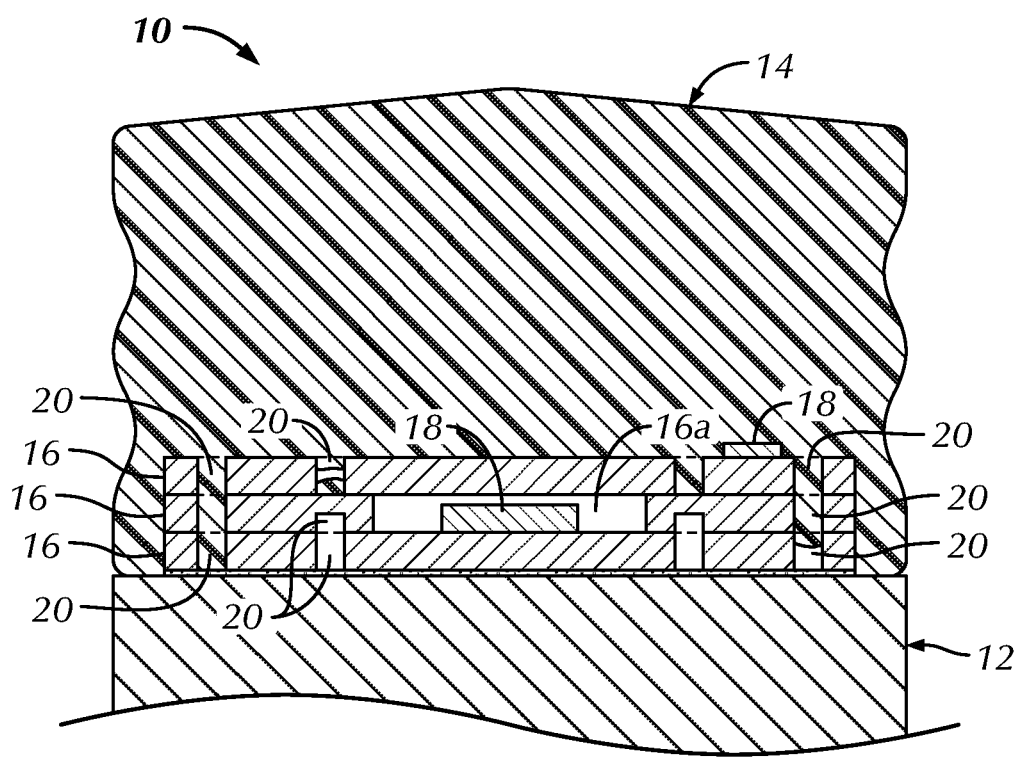
FIG. 6 is a cross-sectional elevational view of the plunger assembly of FIG. 5, taken along sectional line 6-6 of FIG. 5.

Embedded within the elastomeric plunger 14, as shown schematically in FIGS. 3-6, is at least one printed circuit board ("PCB") 16, e.g., multilayered, single layer or a combination thereof. The rigidity of the at least one PCB 16 serves as a rigid core for the elastomeric plunger 14, i.e., operating as a structural backbone of the plunger 14. In the illustrated embodiment, three PCBs 16 in series are embedded within the elastomeric plunger 14, but the disclosure is not so limited. That is, one, two or more than three PCBs 16 may be embedded within the plunger 14. In configurations with multiple PCBs 16, the PCBs 16 may be axially spaced apart by spacers 15 (FIGS. 3, 4), such as, for example, by standoffs. In one embodiment, the standoffs 15 may be constructed of an electrically conductive material, such as, without limitation, metal, which may assist in providing power, ground or electric communication between the PCBs 16. Alternatively, the standoffs 15 may be constructed of a non-conductive material, such as, without limitation, a polymer. Cables, wires or other conductors (not shown) may be employed to provide electric communication between the PCBs 16. Alternatively, the PCBs 16 may be stacked directly upon one another, i.e., mounted or laminated flush with neighboring PCB(s) 16 (FIGS. 5, 6). As should be understood by those of ordinary skill in the art, where more than two PCBs 16 are embedded within the elastomeric plunger 14, a combination of stacked and spaced PCBs 16 may be employed. As also should be understood, the PCBs 16 may be constructed in varying shapes and sizes with respect to one another.

As shown schematically in FIGS. 3-6, at least one electronic component 18 may be electrically connected with the at least one PCB 16 in a manner well understood by those of ordinary skill in the art. For example, without limitation, the electronic component(s) 18 may take the form of at least one processor, sensor, battery, signal conditioning circuit, receiver/transmitter, memory, a combination thereof, or the like. In the illustrated embodiment, some, or all, of the electronic component(s) 18 may also be embedded within the elastomeric plunger 14. For example, an electronic component 18 may be mounted upon a PCB 16. Alternatively, as shown best in FIGS. 4 and 6, a PCB 16 having an aperture 16a therein, e.g., an annular PCB 16, may be employed, and an electronic component 18 may be placed within the aperture 16a. As also should be understood, where more than one PCB 16 is employed, the different PCBs 16 may be constructed in differing geometries, for example, to provide spaces for mounting electronic components 18. In one non-limiting embodiment, for example, some, or all, of the PCB(s) 16 may be disk shaped. As also should be understood by those of ordinary skill in the art, multiple electronic components 18 may be mounted upon a combination of the same or different PCBs 16.

The PCB(s) 16 and the electronic component(s) 18 may be constructed of materials exhibiting high purity and compatible construction materials to minimize extractable compounds. For example, lead-free solder may be utilized, but the disclosure is not so limited. Embedding the PCB(s) 16 and the electronic component(s) 18 within the elastomeric plunger 14 also minimizes contact with the substance/material within the reservoir 56, 156 or 66. The elastomeric plunger 14, the PCB(s) 16 and/or the electronic component(s) 18 may also be coated to enable stability and substance contact compatibility. Non-limiting examples of coatings include amorphous fluoropolymers, such as CYTOP® manufactured by AGC Chemicals, or poly(p-xylylene) polymers, such as Parylene coatings manufactured by Specialty Coating Systems Inc. Alternatively, other compatible vapor deposited or liquid-based coatings, which provide moisture and/or vapor barriers, may be utilized, in order to protect the substance to be administered within the reservoir and the electronic component(s) 18 from one other.

The elastomeric plunger 14 is connected to the distal end 12a of the plunger rod 12 via securement of the PCB(s) 16 to the distal end 12a of the plunger rod 12. For example, as shown in FIGS. 3 and 4, the plunger rod 12 may include at least one mounting rod projecting distally from the distal end 12a thereof and into engagement with at least one PCB 16. In the illustrated embodiment of FIGS. 3 and 4, the standoffs 15 also operate as the mounting rods, which project from the distal end 12a of the plunger rod 12 and into engagement with the PCBs 16. In one non-limiting configuration, the standoffs 15 may include respective hooks (see FIGS. 8, 9) to capture the PCB(s) 16 and make electrical contact therewith. Alternatively, in another non-limiting configuration, the standoffs 15 may have deformable locking tabs (not shown) to capture the PCB(s) 16. In one non-limiting configuration, the standoffs 15 may be integrally formed with the plunger rod 12, i.e., monolithic therewith, and constructed of the same material, but the disclosure is not so limited. As should be understood, the standoffs 15 may be utilized to secure the plunger rod 12 with spaced or stacked PCBs 16, or a combination thereof. Conversely, the mountings rods extending from the distal end 12a of the plunger rod 12 and securing the PCBs 16 may be separate from the standoffs 15 spacing the PCBs 16 apart. Additionally, or alternatively, as shown in FIGS. 5 and 6, the PCB(s) 16 (stacked, spaced or a combination thereof) and/or the elastomeric plunger 14 may be secured directly to the distal end 12 of the plunger rod 12, e.g., via adhesive or the like.

As should be understood by those of ordinary skill in the art, however, further forms of securement of the PCB(s) 16 to the plunger rod 12, currently known or that later become known, may be employed. For example, a PCB 16 having an aperture 16a therein may be employed, permitting the PCB 16 to assemble around the distal end 12a of the plunger rod 12. As other non-limiting examples, the PCB(s) 16 may be attached to the plunger rod 12 by press-fitting (not shown) or by threading (not shown). For example, an inner edge of PCBs 16 with apertures 16a may have notches arranged in a helical orientation from board to board to allow the attached PCBs 16 to be threaded into female threads (not shown) of a plunger rod 12. Alternatively, the PCBs 16 may be keyed (not shown) and slidable into a corresponding notch (not shown) of a plunger rod 12.

In one embodiment, the PCB(s) 16 (with the attached electronic component(s) 18) may be co-molded with the elastomeric plunger 14, although the elastomeric plunger 14 may alternatively be molded separately and the PCB(s) 16 subsequently embedded. When multiple PCBs 16 are employed, and where some of the PCBs 16 are spaced apart, elastomer of the elastomeric plunger 14 may flow around, and between, the PCBs 16, i.e., into the spaces between the PCBs 16, during the molding process and cure, providing a robust attachment between the PCBs 16 and the elastomeric plunger 14, e.g., prevent movement of the PCBs 16 relative to the elastomeric plunger 14 and prevent rotation of the plunger 14 relative to the PCBs 16. As shown best in FIGS. 4 and 6, the PCB(s) 16 may include at least one via 20, e.g., open (a through-hole or channel extending entirely through a PCB 16) or blind (a recess within a PCB 16 having a closed end and an open end). In the illustrated embodiment, several vias 20 are employed, but the disclosure is not so limited. Such vias 20, and/or a central aperture 16a, may place the gaps/spaces between PCBs 16 in fluid communication with one another. In such configurations, elastomer may advantageously also flow through at least a portion of at least one of the vias 20 during the molding process and cure, further solidifying the securement between the PCBs 16 and the elastomeric plunger 14, as well as potting the electronic component(s) 18. That is, the electronic component(s) 18 may also be positioned within vias 20. In alternative configurations, empty gaps/spacing between PCBs 16, and/or empty vias 20, may be occupied with air, providing a route to sterilize the interior of the elastomeric plunger 14 with a gas in a manner well understood by those of ordinary skill in the art.

As should be understood by those of ordinary skill in the art, the flow of elastomer between the PCBs 16 may be accomplished through a variety of traditional processes. Some non-limiting examples include over-molding, injection molding, compression molding, and dip-coating in a low-viscosity polymer mixture (curable or solvent-cast). Alternatively, the PCBs 16 may be formed into a plunger mold. Additionally, the electronic component(s) 18 may be assembled into a pre-formed elastomer matrix and rely on either pre-shaped components capable of interpenetrating, or viscoelastic flow of the cured/solidified material into those spaces. To preserve the cleanliness requirements of the finished components, aseptic assembly conditions may be required. As one non-limiting example, the elastomeric component may need to be washed/sterilized separately from the PCB/electronic component and then be assembled prior to use. As should be understood, sterilization options may be selected depending on the PCB(s) 16 and electronic component(s) 18 employed. For example, a temperature sensitive PCB(s) 16 and/or electronic component(s) 18 may require a compatible sterilization method, such as the use of gamma radiation or ethylene oxide gas rather than steam sterilization.

FIG. 7 illustrates a second embodiment of an elastomeric plunger 114. The reference numerals of the second embodiment are distinguishable from those of the above-described first embodiment (FIGS. 1-6) by a factor of one-hundred (100), but otherwise indicate the same elements as indicated above, except as otherwise specified. The elastomeric plunger 114 of the present embodiment is substantially similar to that of the earlier embodiment. Therefore, the description of certain similarities and modes of operation between the embodiments may be omitted herein for the sake of brevity and convenience, and, therefore, is not limiting.

One difference of the elastomeric plunger 114 shown in FIG. 7 over the elastomeric plunger 14 is that the elastomeric plunger 114 is not secured or otherwise connected to a plunger rod 12. Rather, the elastomeric plunger 114 may be positioned stationary, i.e., at a fixed location, within the reservoir 156 of the vessel 150. Similarly to the elastomeric plunger 14, the elastomeric plunger 114 is also configured to sealingly engage the sidewall of the reservoir 156 when inserted therein and includes at least one PCB 116 embedded within and at least one electronic component 118 electrically connected with the at least one PCB 116. In the illustrated configuration of FIG. 7, the PCBs 116 are spaced apart by spacers 115, but the disclosure is not so limited (as described with respect to PCBs 16). As shown in FIG. 7, the elastomeric plunger 114 further includes at least one through-channel 122, extending through the elastomeric plunger 114, fluidly connecting a portion of the reservoir 156 on one side of the plunger 114 with a portion of the reservoir 156 on the opposing side of the plunger 114. Rigidity of the plunger 114, e.g., provided by the at least one PCB 116 operating as a rigid core of the plunger 114, assists in preventing collapse of the through-channel 122 due to the pressure within the reservoir 156 during use.

In one embodiment, an electronic component 118 of the plunger 114 may take the form of a flow sensor to capture information on the quantity of material, e.g., medicament, administered, as well as to assist in determining the duration of administration. Non-limiting examples of flow sensors include turbine meters, paddle wheel meters, differential pressure meters (e.g. venturi meter), thermal mass flow meters, elastic filament flow meters and coriolis flow meters or the like. Turbine meters may advantageously provide potential power generation which may be utilized for other electronic components. Electronic sensors, such as elastic filament meters, advantageously lack moving parts, which minimizes potential for malfunction. Elastic filament velocimetry (EFV) may also be advantageous due to the insensitivity of the surface chemistry, thereby being compatible with a variety of coatings/treatments, as well as being low cost and miniature using existing semiconductor fabrication techniques. As should be understood, the flow sensor may be mounted on a PCB 116 as an inline flow meter (relative to the channel 122) or as a side-mounted flow meter (relative to the channel 122).

In one configuration, as shown in FIG. 7, the elastomeric plunger 114 may take the form of a second plunger located within the reservoir 156 between the plunger 14 at the distal end 12a of the plunger rod 12 and the distal end of the vessel 150, e.g., proximate the distal end of the reservoir 156, which, advantageously, is a highly tamper resistant location. The electronic component(s) 18 of the elastomeric plunger 14 secured to the distal end of the plunger rod 12 may be configured to electronically communicate with the electronic component(s) 118 of the plunger 114. For example, as shown in FIG. 7, the electronic component(s) 118 may operate as a fixed-location component, i.e., positioned within the stationary plunger 114, configured to interact with either the moving electronic component(s) 18 within the plunger 14 or with external devices (not shown). Generally, the distance therebetween may be calculated as a function of transmitted energy, such as, for example, via magnetic fields, radio frequency, acoustic waves, photons, a combination thereof, or the like. For example, changes in inductance, resonant power transfer, magnetic sensing (e.g., magnet/magnetic material/reed switch in the different plungers 14, 114), and absorbance differences may be correlated to distance changes, but the disclosure is not so limited. The calculated distance measurement may then be correlated to dosing, for example. In other non-limiting examples, the electronic components 18, 118 may take the form of accelerometers in order to derive spatial information. Employing electronic components 18, 118, in the two plungers 14, 114, respectively, enables optical spectroscopy therebetween, i.e., placement of an electronic component operating as a source and another operating as a detector. Advantageously, such configuration may improve signal to noise ratios by decreasing the path length as compared to a system relying on reflection (when utilizing a single plunger). Alternatively, or additionally, optical spectroscopy may be employed within the same plunger. For example, electronic components 118 may be placed on opposite sides of the channel 122 of the plunger 114 and communication as source and detector.

Further advantageously, stationary placement of the elastomeric plunger 114 within the reservoir 156 of the vessel 150, e.g. a plunger 114 having a "chevron" shaped cross-section, placed at a distal end of the reservoir 156, may also be configured to reduce dead-space within the reservoir 156 and maximize dosage. For example, as shown in FIG. 7, the proximal end of the elastomeric plunger 114 is configured, e.g., shaped, to mate with the distal surface of the elastomeric plunger 14 to minimize dead-space therebetween. Alternatively, without limitation, the proximal end of the elastomeric plunger 114 and the distal end of the elastomeric plunger 14 may both be generally planar. Additionally, the distal end of the elastomeric plunger 114 may also be configured to mate with the distal end of the reservoir 156, to further minimize dead-space. Additional advantages of the stationary placement of the elastomeric plunger 114 include the ability to utilize larger reservoirs 156 with smaller dosages due to the presence of the plunger 114.

Figure 8:
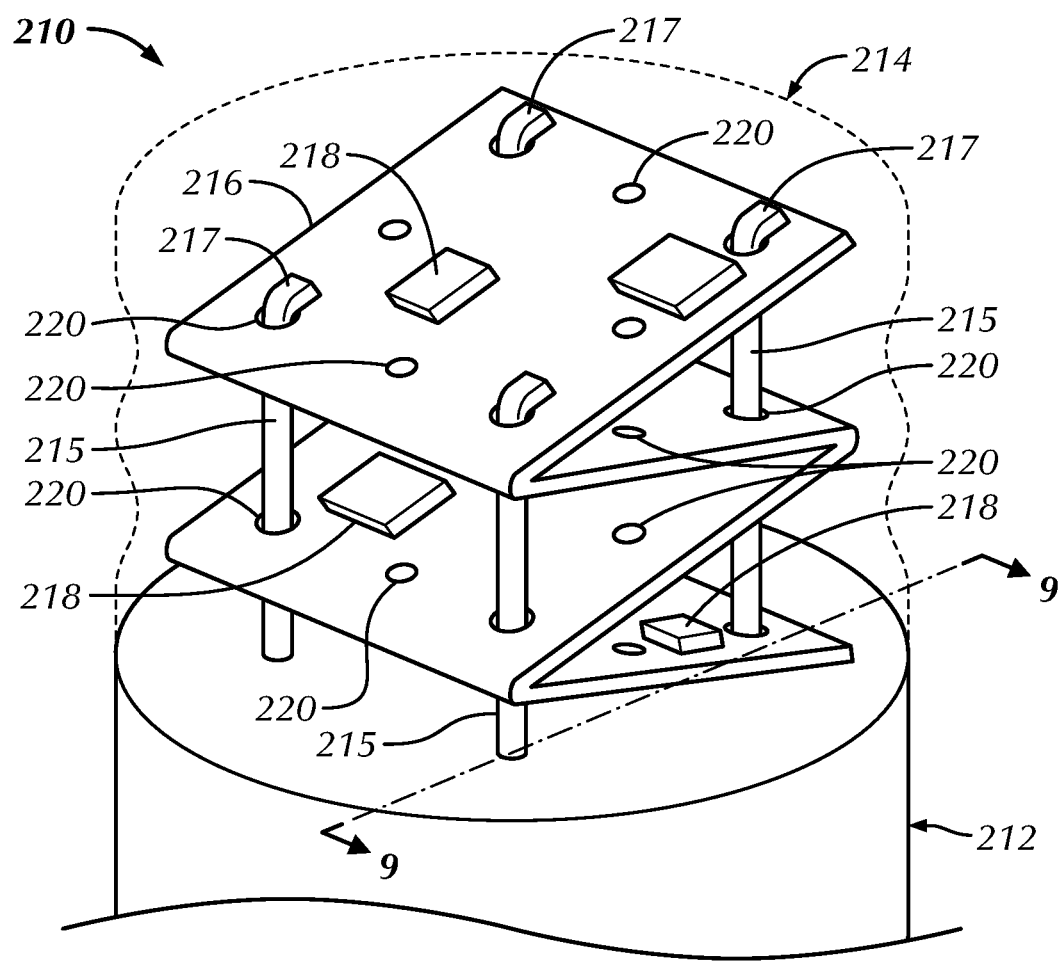
FIG. 8 is an enlarged, partial perspective view of a plunger assembly according to a third embodiment of the present disclosure.
Figure 9:
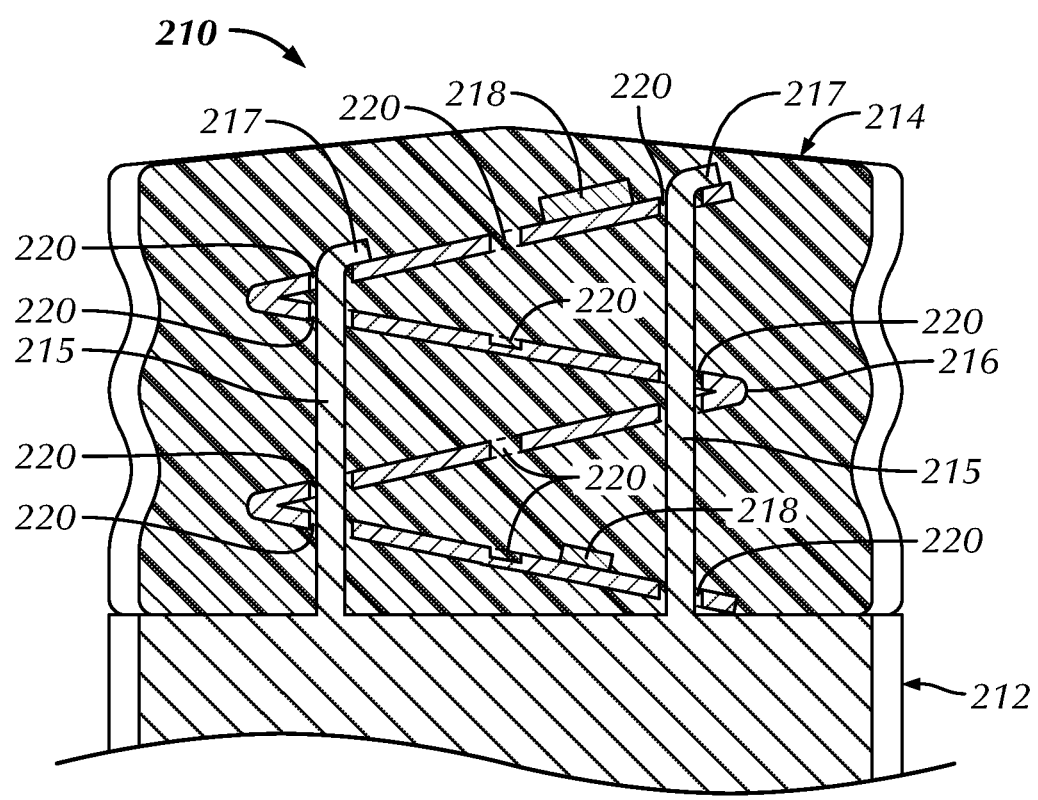
FIG. 9 is a cross-sectional elevational view of the plunger assembly of FIG. 8, taken along sectional line 9-9 of FIG. 8.

FIGS. 8-9 illustrate a plunger assembly 210 according to a third embodiment. The reference numerals of the third embodiment are distinguishable from those of the above-described first embodiment (FIGS. 1-6) by a factor of two-hundred (200), but otherwise indicate the same elements as indicated in the first embodiment, except as otherwise specified. The plunger assembly 210 of the present embodiment is substantially similar to that of the first embodiment. Therefore, the description of certain similarities and modes of operation between the embodiments may be omitted herein for the sake of brevity and convenience, and, therefore, is not limiting.

One difference of the plunger assembly 210 shown in FIGS. 8 and 9 over the plunger assembly 10 is that PCB 216 may take the form of an elongated flexible circuit board. In the illustrated embodiment, the PCB 216 is foldable onto itself, e.g., in an accordion-like manner, and attachable to the mounting rods 215 of the plunger rod 212. As shown, the mounting rods 215 may extend through apertures or open vias 220 that are positioned to become axially aligned when the PCB 216 is folded. In the illustrated embodiment, the mounting rods 215 include distal hooks 217 to capture the PCB 216, but the disclosure is not so limited. Other means, currently known or that later become known, may additionally or alternatively be employed to secure the mounting rods 215 with the PCB 216 and/or the elastomeric plunger 214. As also should be understood by those of ordinary skill in the art, the PCB 216 may be otherwise wrapped around the distal end of the plunger rod 212. Similarly to the elastomeric plunger 14, the elastomeric plunger 214 also includes at least one electronic component 218 electrically connected with the flexible PCB 216.

It will be appreciated by those skilled in the art that changes could be made to the embodiments described above without departing from the broad inventive concepts thereof. For example, the PCB(s) and attached electronic component(s) may be embedded in a tip-cap (not shown), needle shield (not shown), or needle shield cover (not shown). By including these electronic components into drug-contact-components, other than plungers, additional functionality can be realized. For example, for anti-tamper/anti-counterfeit purposes, electronic components in the stopper/tip cap/needle shield could assist by serialization of those components, and, thereafter, record tampering (e.g. attempted refill through the needle/connector), prevent removal from the syringe (e.g. prevent administration), and/or disable the cap for future use (e.g. prevent re-use). Employing the electronic components in an easy-to-access location on the exterior of a syringe may also be advantageous in certain applications. For example, PCB(s) placed in a needle shield or tip cap are generally stabilized at a pre-defined location. Consistent location would facilitate integration with an external device. Such integration could allow for the identification of the drug product, transfer information such as the intended patient, and/or cause a general-purpose administration device to perform a specific administration routine. Additionally, with the electronic components being located on the exterior of a syringe or cartridge, this provides an easier means of power/data transfer (e.g. via exposed contacts). The PCB(s) and attached electronic component(s) may also be embedded in a stopper, and used as an indicator of pharmaceutical integrity (e.g. spectroscopy), and the quality of the environment (e.g. oxygen concentration). It is understood, therefore, that this invention is not limited to the particular embodiments disclosed, but it is intended to cover modifications within the spirit and scope of the present disclosure, as set forth in the appended claims.

I claim:

1. A plunger assembly configured for slidable advancement through a reservoir of a vessel containing a material to be administered, the plunger assembly comprising:
   a plunger rod having a distal end configured to be inserted into the reservoir;
   an elastomeric plunger extending from the distal end of the plunger rod and configured to sealingly engage a sidewall of the reservoir;
   at least one printed circuit board embedded within the elastomeric plunger, the at least one printed circuit board including at least one of a via and/or a recess and at least a portion of the elastomeric plunger being disposed within the at least one of the via and/or the recess; and
   at least one electronic component electrically connected with the at least one printed circuit board.

2. The plunger assembly of claim 1, wherein the at least one printed circuit board comprises a plurality of printed circuit boards spaced apart by spacers.

3. The plunger assembly of claim 2, wherein at least one of the spacers is electrically conductive.

4. The plunger assembly of claim 2, wherein the elastomeric plunger extends around and between the spaced apart printed circuit boards.

5. The plunger assembly of claim 1, wherein the at least one printed circuit board comprises a plurality of stacked printed circuit boards.

6. The plunger assembly of claim 1, wherein the plunger rod includes at least one mounting rod projecting distally from the distal end thereof and into engagement with the at least one printed circuit board to secure the elastomeric plunger with the plunger rod.

7. The plunger assembly of claim 1, wherein the at least one electronic component is embedded within the elastomeric plunger.

8. The elastomeric plunger of claim 1, wherein the at least one electronic component comprises at least one of a processor, a sensor, a battery, a signal conditioning circuit, a receiver, a transmitter, and/or a memory.

9. The elastomeric plunger of claim 1, wherein the at least one electronic component is mounted on the at least one printed circuit board.

10. The elastomeric plunger of claim 1, wherein the at least one printed circuit board is disk shaped.

11. The elastomeric plunger of claim 1, wherein the at least one of the via and/or the recess includes a plurality of the vias and/or the recesses.

12. An assembly comprising the plunger assembly of claim 1, and a vessel containing a material.

13. The assembly of claim 12, wherein the vessel includes a proximal end having an opening and a distal end, the plunger rod being inserted through the opening such that the distal end of the plunger rod is positioned within the reservoir, the plunger assembly further comprising:
   a second elastomeric plunger located within the reservoir between the distal end of the plunger rod and the distal end of the vessel, the second elastomeric plunger comprising at least one printed circuit board embedded within the second elastomeric plunger, at least one electronic component electrically connected with the at least one printed circuit board, and at least one channel extending through the second elastomeric plunger and fluidly connected to the reservoir, wherein the at least one electronic component of the elastomeric plunger is configurated to electronically communicate with the at least one electronic component of the second elastomeric plunger.

14. The assembly of claim 13, wherein the vessel is a syringe or a cartridge.

15. An elastomeric plunger configured to be positioned stationary within a reservoir of a vessel containing a material to be administered, the elastomeric plunger being configured to sealingly engage a sidewall of the reservoir, the elastomeric plunger comprising:
   at least one printed circuit board embedded within the elastomeric plunger;
   at least one electronic component electrically connected with the at least one printed circuit board; and
   at least one channel extending through the elastomeric plunger fluidly connected with the reservoir,
   wherein the at least one printed circuit board includes at least one of a via and/or a recess and at least a portion of the elastomeric plunger is disposed within the at least one of the via and/or the recess.

16. The elastomeric plunger of claim 15, wherein the at least one printed circuit board comprises a plurality of printed circuit boards spaced apart by spacers.

17. The elastomeric plunger of claim 16, wherein at least one of the spacers is electrically conductive.

18. The elastomeric plunger of claim 16, wherein the elastomeric plunger extends around and between the spaced apart printed circuit boards.

19. The elastomeric plunger of claim 15, wherein the at least one printed circuit board comprises a plurality of stacked printed circuit boards.

20. The elastomeric plunger of claim 15, wherein the at least one electronic component is embedded within the elastomeric plunger.

* * * * *